United States Patent [19]

Charles et al.

[11] Patent Number: 5,683,700
[45] Date of Patent: Nov. 4, 1997

[54] EXPRESSION OF RECOMBINANT PROTEINS IN ATTENUATED BACTERIA

[75] Inventors: Ian George Charles; Steven Neville Chatfield; Neil Fraser Fairweather, all of Kent, England

[73] Assignee: Glaxo Wellcome Inc., Research Triangle Park, N.C.

[21] Appl. No.: 469,507

[22] Filed: Jun. 6, 1995

Related U.S. Application Data

[62] Division of Ser. No. 354,776, Dec. 12, 1994, Pat. No. 5,547,664, which is a continuation of Ser. No. 246,773, May 20, 1994, abandoned, which is a continuation of Ser. No. 81,361, filed as PCT/GB92/00387, Mar. 5, 1992 published as WO92/15689, Sep. 17, 1992, abandoned.

[30] Foreign Application Priority Data

Mar. 5, 1991 [GB] United Kingdom ............... 9104596
Oct. 4, 1991 [GB] United Kingdom ............... 9121208

[51] Int. Cl.$^6$ .................................................. A61K 39/00
[52] U.S. Cl. .................. 424/200.1; 424/93.2; 435/252.3; 435/252.8
[58] Field of Search ............... 435/252.3, 320.1, 435/69.7, 252.8; 536/24.1; 935/41, 43, 65, 72; 424/200.1, 234.1, 258.1, 282.1, 93.2, 192.1

[56] References Cited

U.S. PATENT DOCUMENTS

4,837,151 6/1989 Stocker ............................... 424/200.1
4,963,482 10/1990 Birkmann et al. ..................... 435/69.1

FOREIGN PATENT DOCUMENTS

| | | |
|---|---|---|
| 2015046 | 10/1990 | Canada . |
| 0 285 152 | 10/1988 | European Pat. Off. . |
| 0322 237 | 6/1989 | European Pat. Off. . |
| 0 357 208 | 3/1990 | European Pat. Off. . |
| 0 400 958 | 12/1990 | European Pat. Off. . |
| WO 91/15572 | 10/1991 | WIPO . |
| WO 92/15688 | 9/1992 | WIPO . |

OTHER PUBLICATIONS

Aliabadi et al., "Oxygen-regulated stimulaons of *Salmonella typhimurium* identified by Mu d(Ap lac) operon fusions", J. Bacteriol. 165: 780–786, Mar. 1986.
Everest et al, "Expression of LacZ from the htrA, nirB and groE promoters in a Salmonella vaccine strain: Influence of growth in mammalian cells", FEMS Microbiology Letters 126:97–102 (1995).
Chatfield et al, "Use of the nirB Promoter to Direct the Stable Expression of Heterologous Antigens in Salmonella oral vaccine strains: Development of a Single-Dose Oral Tetanus Vaccine", Bio/Technology 10:888–892 (1992).
Fairweather et al, "Use of Live Attenuated Bacteria To Stimulate Immunity", Res. Microbiol 141:769–773 (1990).
Jayaraman et al, "Mutational analysis of the nucleotide sequence at the FNR-dependent nirB promoter in *Escherichia coli*", Nucleic Acids Research 17(1):135–145 (1989).

Jayaraman et al, "Location and Sequence of the Promoter of the Gene for the NADH-dependent Nitrite Reductase of *Escherichia coli* and its Regulation by Oxygen, the Fnr Protein and Nitrite", J. Mol. Biol. 196:781–788 (1987).
Jayaraman et al, "The nirB promoter of *Escherichia coli*: location of nucleotide sequences essential for regulation by oxygen, the FNR protein and nitrite", Molecular Microbiology 2(4):527–530 (1988).
Khosla et al, "Expression of Recombinant Proteins in *Escherichia coli* Using an Oxygen-Responsive Promoter", Bio/Technology 8:554–558 (1990).
Makoff et al, "Expression of Tetanus Toxin Fragment C in *E. coli*: Its Purification and Potential Use as a Vaccine", Bio/Technology 7:1043–1045 (1989).
Oxer et al, "High level heterologous expression in *E. coli* using the anaerobically-activated nirB promoter", Nucleic Acids Research, 19(11)2889–2892 (1991).
Bell et al, "Cloning of binding sequences for the *Escherichia coli* transcription activators, FNR and CRP: location of bases involved in discrimination between FNR and CRP", Nucleic Acids Research 17(10):3865–3874 (1989).
Khosla et al, "Characterization of the Oxygen-Dependent Promoter of the Vitreoscilla Hemoglobin Gene in *Escherichia coli*", Journal of Bacteriology 171(11):5995–6004 (1989).
Maskell et al, "*Salmonella typhimurium* aroA mutants as carriers of the *Escherichia coli* heat-labile enterotoxin B subunit to the murine secretory and systemic immune systems", Microbial Pathogenesis 2:211–221 (1987).
Nakayama et al, "Construction of an ASD$^+$ Exression-Cloning Vector: Stable Maintenance and High Level Expression of Cloned Genes in a Salmonella Vaccine Strain", Bio/Technology 6:693–697 (1988).
Tite et al, "Anti-viral immunity induced by recombinant nucleoprotein of Influenza A virus", Immunology 70:540–546 (1990).
Hone et al, "A chromosal integration system for stabilization of heterologous genes in Salmonella based vaccine strains", Microbial Pathogenesis 5:407–418 (1988).
Strugnell et al, "Stable expression of foreign antigens from the chromosome of *Salmonella typhimurium* vaccine strains", Gene 88:57–63 (1990).
Peakman et al, "Nucleotide sequence, organisation and structural analysis of the products of genes in the nirB—cysG region of the *Escherichia coil* K–12 chromosome" Eur. J. Biochem. 191:315–323 (1990).

(List continued on next page.)

*Primary Examiner*—James Ketter
*Assistant Examiner*—Irem Yucel
*Attorney, Agent, or Firm*—Nixon & Vanderhye, P.C.

[57] ABSTRACT

The invention concerns a method of prophylactically treating a host against infection by a microorganism, which method comprises administering to the host an attenuated *Salmonella bacterium* which contains a nirB promoter operably linked to a DNA sequence encoding a heterologous protein. The heterologous protein is expressed in the host and induces in the host an immune response against the microorganism.

7 Claims, 3 Drawing Sheets

OTHER PUBLICATIONS

Cole, "Cytochrome $C_{552}$ and Nitrite Reduction in *Escherichia Coli*", Biochimica Et Biophyssica Acta 162:356–368 (1968).

Chatfield et al, "Live Salmonella as vaccines and carriers of foreign antigenic determinants", Vaccine 7:495–498 (1989).

Dorman et al, "Characterization of Porin and ompR Mutants of a Virulent Strain of *Samonella typhimurium*: ompR Mutants Are Attenuated In Vivo", Infection and Immunity 57(7):2136–2140 (1989).

Buckmeier et al, "Recombination–deficient mutants of *Salmonella typhimurium* are avirulent and sensitive to the oxidative burst of macrophages", Molecular Microbiology 7(6):933–936 (1993).

Miller et al, "A two–component regulatory system (phoP phoQ) controls *Salmonella typhimurium* virulence", Proc. Natl. Acad. Sci. USA, 86:5054–5058 (1989).

O'Callaghan et al, "Characterization of Aromatic–and Purine–Dependent *Salmonella typhimurium*: Attenuation, Persistance, and Ability to Induce Protective Immunigy in BALB/c Mice", Infection and Immunity 56(2):419–423 (1988).

Tacket et al, "Comparison of the Safety and Immunogenicity of ΔaroC ΔaroD and Δcya Δcry *Salmonella typhi* Strains in Adult Volunteers", Infection and Immunity 60(2):536–541 (1992).

Chatfield et al, "Role of ompR–Dependent Genes in *Salmonella typhimurium* Virulence: Mutants Deficient in Both OmpC and OmpF Are Attenuated In Vivo", Infection and Immunity 59(1):449–452 (1991).

Fairweather et al, Infection & Immunity 58(5):1323–1326 (1990).

Bell et al, Molec. Microbiol 4(10):1753–1763 (1990).

Ronson et al, Cell 49:579–581 (1987).

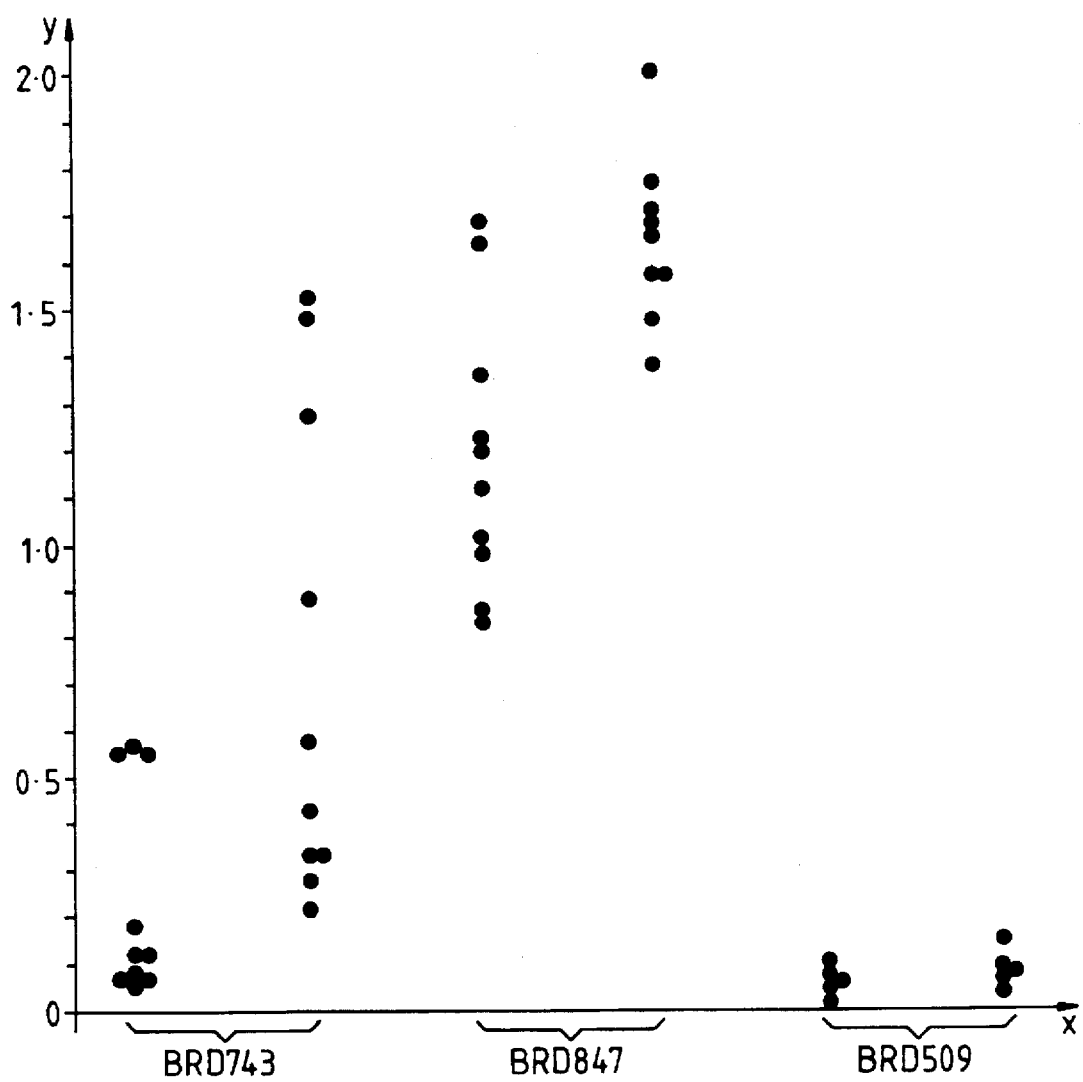

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 68 base pairs
( B ) TYPE: nucleic acid -continued ( C ) STRANDEDNESS: double
( D ) TOPOLOGY: linear ( i i ) MOLECULE TYPE: DNA (genomic)

( x i ) SEQUENCE DESCRIPTION: SEQ ID NO: 1:

AATTCAGGTA AATTTGATGT ACATCAAATG GTACCCCTTG CTGAATCGTT AAGGTAGGCG 60

GTAGGGCC 68

( 2 ) INFORMATION FOR SEQ ID NO: 2:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 2:

CTACCGCCTA CCTTAACGAT TCAGCAAGGG GTACCATTTG ATGTACATCA AATTTACCTG 60

EXPRESSION OF RECOMBINANT PROTEINS IN ATTENUATED BACTERIA

This is a divisional of application Ser. No. 08/354,776, filed Dec. 12, 1994, U.S. Pat. No. 5,549,664 which is a continuation of Ser. No. 08/246,773, filed May 20, 1994 (abandoned), which is a continuation of Ser. No. 08/081, 361, filed as PCT/GB92/00387, Mar. 5, 1992 published as WO92/15689, Sep. 17, 1992 (abandoned).

This invention relates to attenuated bacteria capable of expressing a heterologous protein, to their preparation and to vaccines containing them.

Virulent strains of Salmonella can be attenuated by introducing specific mutations into genes required for survival and growth in vivo. Attenuated variants which establish self limiting, clinically insignificant infections can be considered as potential live oral vaccines against Salmonella infections. Ty21a is an attenuated variant of *Salmonella typhi*, which harbours mutations in galE and other unknown attenuating lesions, and is licensed for use in many countries as a live oral typhoid vaccine.

More recently genetically defined Salmonella strains harbouring individual specific mutants in different genes have been tested as experimental oral vaccines in several target species. For example, *Salmonella aro* mutants, which have an auxotrophic requirement for several aromatic compounds, have been shown to be effective oral vaccines in mice, sheep, cattle, chickens and more recently they have been shown to be attenuated and immunogenic in volunteers. Salmonella double aro mutants are disclosed in EP-A-0322237. Salmonella cya crp double mutants are also, effective oral vaccines.

As well as being vaccines in their own right against salmonellosis, attenuated Salmonellae can be considered as carriers of heterologous antigens to the immune oral system. This is because Salmonellae can be delivered via the oral route and are potent immunogens being able to stimulate systemic and local cellular and antibody responses. Heterologous antigens from bacteria, viruses and parasites can be delivered to the host using Salmonella vaccines.

One potentially serious drawback in using these live vaccines for antigen delivery relates to problems with the stability of the foreign antigen expression in vivo. Unregulated expression of high levels of a foreign protein in bacteria from multiple copy plasmids usually results in rapid loss of the plasmid or expressed gene from the cells. This problem can be controlled in fermenters by using inducible promoter systems such as trp or lac to allow the controlled induction of gene expression when the appropriate biomass has been achieved. Obviously these promoters can not be induced by exogenously applied inducers such as PP or IPTG when bacteria are growing in host tissues during the self-limited growth following vaccination.

In vivo plasmid instability during vaccination with live bacterial vectors has in fact been reported by many workers (Maskell et al, Microb.Path 2, 295–305, 1987; Nakayama et al, Bio/technology 6, 693–697, 1988; Tite et al, Immunology 70, 540–546, 1990). A number of approaches have been taken to overcome the problem including the use of integration systems for expression of the heterologous antigen from the bacterial chromosome (Hone et al, Microbiol. Path. 5, 407–418, 1988; Strugnell et al, Gene 88, 57–63, 1990). However, this approach is only suitable for use with some antigens since expression levels are often quite low (Maskell et al, 1987). Nakayama et al described the use of linking an essential gene to the expression plasmid for stabilizing in vivo expression. Although this is a highly effective approach, it does not prevent the generation of plasmid free variants but simply ensures they do not survive. Further stable but constitutive high level expression of a foreign antigen in a Salmonella vaccine strain could slow down the growth rate and hence potentially effect the immunogenicity of the live vaccine.

According to the present invention, there is provided an attenuated bacterium which is capable of expressing a heterologous protein, the expression of the heterologous protein being under the control of a promoter whose activity is induced by anaerobic conditions.

Stable expression of the heterologous protein can be obtained in vivo. The attenuated bacterium can therefore be used as a vaccine. Any suitable bacterium may be employed, for example a Gram-negative bacterium. Some Gram-negative bacteria such as Salmonella invade and grow within eucaryotic cells and colonise mucosal surfaces.

The attenuated bacterium may therefore be selected from the genera Salmonella, Bordetella, Vibrio, Haemophilus, Neisseria and Yersinia. Alternatively, the attenuated bacterium may be an attenuated strain of Enterotoxigenic *Escherichia coli*. In particular the following species can be mentioned: *S. typhi*—the cause of human typhoid; *S. typhimurium*—the cause of salmonellosis in several animal species; *S. enteritidis*—a cause of food poisoning in humans; *S. choleraesuis*—a cause of salmonellosis in pigs; *Bordetella pertussis*—the cause of whooping cough; *Haemophilus influenzae*—a cause of meningitis; *Neisseria gonorrhoeae*—the cause of gonorrhoea; and Yersinia—a cause of food poisoning.

Attenuation of the bacterium may be attributable to a non-reverting mutation in a gene in the aromatic amino acid biosynthetic pathway of the bacterium. There are at least ten genes involved in the synthesis of chorismate, the branch point compound in the aromatic amino acid biosynthetic pathway. Several of these map at widely differing locations on the bacterial genone, for example aroA (5-enolpyruvylshikimate-3-phosphate synthase), aroC (chorismate synthase), aroD (3-dihydroquinate dehydratase) and aroE (shikimate dehydrogenase). A mutation may therefore occur in the aroA, aroC, aroD or aroE gene.

Preferably, however, an attenuated bacterium harbours a non-reverting mutation in each of two discrete genes in its aromatic amino acid biosynthetic pathway. Such bacteria are disclosed in EP-A-0322237. Double aro mutants which are suitable are aroA aroC, aroA aroD and aroA aroE mutant bacteria. Other bacteria having mutations in other combinations of the aroA, aroC, aroD and aroE genes are however useful. Particularly preferred are Salmonella double aro mutants, for example double aro mutants of *S.typhi* or *S.typhimurium*, in particular aroA aroC, aroA aroD and aroA aroE mutants.

Alternatively, the attenuated bacterium may harbour a non-reverting mutation in a gene concerned with the regulation of one or more other genes (EP-A-0400958). Preferably the mutation occurs in the ompR gene or another gene involved in regulation. There are a large number of other genes which are concerned with regulation and are known to respond to environmental stimuli (Ronson et al, Cell 49, 579–581).

This type of attenuated bacterium may harbour a second mutation in a second gene. Preferably the second gene is a gene encoding for an enzyme involved in an essential biosynthetic pathway, in particular genes involved in the pre-chorismate pathway involved in the biosynthesis of aromatic compounds. The second mutation is therefore preferably in the aroa, aroC or aroD gene.

Another type of attenuated bacterium is one in which attenuation is brought about by the presence of a non-reverting mutation in DNA of the bacterium which encodes, or which regulates the expression of DNA encoding, a protein that is produced in response to environmental stress. Such bacteria are disclosed in WO 91/15572. The non-reverting mutation may be a deletion, insertion, inversion or substitution. A deletion mutation may be generated using a transposon.

Examples of proteins that are produced in response to environmental stress include heat shock proteins (which are produced in response to a temperature increase above 42° C.); nutrient deprivation proteins (which are produced in response to levels of essential nutrients such as phosphates or nitrogen which are below that which the microorganism requires to survive); toxic stress proteins (which are produced in response to toxic compounds such as dyes, acids or possibly plant exudates); or metabolic disruption proteins (which are produced in response to fluctuations in for example ion levels affecting the microorganisms ability to osmoregulate, or vitamin or co-factor levels such as to disrupt metabolism).

Preferably a heat shock protein is the one encoded by the htrA gene, also characterised as degP. Other proteins are encoded by genes known to be involved in the stress response such as grpE, groEL, (moPA), dnaK, groES, lon and dnaJ. There are many other proteins encoded by genes which are known to be induced in response to environmental stress (Ronson et al., Cell 49, 579–581). Amongst these the following can be mentioned: the ntrB/ntrC system of $E. coli$, which is induced in response to nitrogen deprivation and positively regulates glnA and nifLA (Buck et al., Nature 320, 374–378, 1986; Hirschman et al., Proc. Natl. Acad. Sci. USA, 82, 7525, 1985; Nixon et al., Proc. Natl. Acad. Sci. USA 83, 7850–7854, 1986, Reitzer and Magansanik, Cell, 45, 785, 1986); the phoR/phoB system of $E. coli$ which is induced in response to phosphate deprivation (Makino et al., J. Mol. Biol. 192, 549–556, 1986b); the cpxA/sfraA system of $E. coli$ which is induced in response to dyes and other toxic compounds (Albin et al., J. biol. Chem. 261 4698, 1986; Drury et al., J. Biol. Chem. 260, 4236–4272, 1985). An analogous system in Rhizobium is dctB/dctD, which is responsive to 4C-discarboxylic acids (Ronson et al., J. Bacteriol. 169, 2424 and Cell 49, 579–581, 1987). A virulence system of this type has been described in Agrobacterium. This is the virA/virG system, which is induced in response to plant exudates (le Roux et al., EMBO J. 6, 849–856, 1987; Stachel and Zambryski., Am. J. Vet. Res 45, 59–66, 1986; Winans et al., Proc. Natl. Acad. Sci. USA, 83, 8278, 1986). Similarly the bvgC-bvgA system in $Bordetella pertussis$ (previously known as vir) regulates the production of virulence determinants in response to fluctuations in Mg2+ and nicotinic acid levels (Arico et al, 1989, Proc. Natl. Acad. Sci. USA 86, 6671–6675).

For use in the form of a live vaccine, an attenuated bacterium should not revert back to the virulent state. The probability of this happening with a mutation in a single DNA sequence is considered to be small. However, the risk of reversion occurring with a bacterium attenuated by the presence of mutations in each of two discrete DNA sequences is considered to be insignificant. A preferred attenuated bacterium is therefore one in which attenuation is brought about by the presence of a mutation in a DNA sequence which encodes, or which regulates the expression of DNA encoding, a protein that is produced in response to environmental stress and by the presence of a mutation in a second DNA sequence.

The second DNA sequence preferably encodes an enzyme involved in an essential auxotrophic pathway or is a sequence whose product controls the regulation of osmotically responsive genes, i.e. ompR, (Infect and Immun 1989 2136–2140). Most preferably, the mutation is in a DNA sequence involved in the aromatic amino acid biosynthetic pathway, more particularly the DNA sequences encoding aroA, aroC or aroD.

Attenuated bacteria may be constructed by the introduction of a mutation into the DNA sequence by methods known to those skilled in the art (Maniatis, Molecular Cloning and Laboratory Manual, 1982). Non-reverting mutations can be generated by introducing a hybrid transposon TnphoA into, for example, $S.typhimurium$ strains. TnphoA can generate enzymatically active protein fusions of alkaline phosphatase to periplasmic or membrane proteins. The TnphoA transposon carries a gene encoding kanamycin resistance. Transductants are selected that are kanamycin resistant by growing colonies on an appropriate selection medium.

Alternative methods include cloning the DNA sequence into a vector, e.g. a plasmid or cosmid, inserting a selectable marker gene into the cloned DNA sequence, resulting in its inactivation. A plasmid carrying the inactivated DNA sequence and a different selectable marker can be introduced into the organisma by known techniques (Maniatis, Molecular Cloning and Laboratory Manual, 1982). It is then possible by suitable selection to identify a mutant wherein the inactivated DNA sequence has recombined into the chromosome of the microorganism and the wild-type DNA sequence has been rendered non-functional in a process known as allelic exchange. In particular, the vector used is preferably unstable in the microorganism and will be spontaneously lost. The mutated DNA sequence on the plasmid and the wild-type DNA sequence may be exchanged by a genetic cross-over event. Additional methods eliminate the introduction of foreign DNA into vaccine strains at the site of mutations and the introduction of antibiotic resistant markers into the strains.

The heterologous antigen which an attenuated bacterium is capable of expressing may for example comprise an antigenic determinant of a pathogenic organism. The antigen may be derived from a virus, bacterium, fungus, yeast or parasite. The heterologous protein therefore typically comprises an antigenic sequence derived from a virus, bacterium, fungus, yeast or parasite. More especially, the antigenic sequence may be derived from a type of human immunodeficiency virus (HIV) such as HTV-1 or HIV-2, hepatitis A or B virus, human rhinovirus such as type 2 or type 14, herpes simplex virus, poliovirus type 2 or 3, foot-and-mouth disease virus, influenza virus, coxsackie virus, the cell surface antigen CD4 and $Chlamydia trachomatis$. The antigen may comprise the CD4 receptor binding site from HIV, for example from HIV-1 or -2. Other useful antigens include $E. coli$ heat labile toxin B subunit (LT-B), $E. coli$ K88 antigens, p.69 protein from $B. pertussis$, tetanus toxin fragment C and antigens of flukes, mycoplasma, roundworms, tapeworms, rabies virus and rotavirus.

A preferred promoter for use in controlling the expression of the heterologous protein is the nirB promoter. The nirB promoter has been isolated from $E. coli$, where it directs expression of an operon which includes the nitrite reductase gene nirB (Jayaraman et al, J. Mol. Biol. 196, 781–788, 1987), and nirD, nirC and cysG (Peakman et al, Eur J. Biochem, 191, 315–323, 1990). It is regulated both by nitrite and by changes in the oxygen tension of the environment, becoming active when deprived of oxygen (Cole, Biochim. Biophys. Acta, 162, 356–368, 1968). Response to anaerobiosis is mediated through the protein FNR, acting as a transcriptional activator, in a mechanism common to many anaerobic respiratory genes.

By deletion and mutational analysis the part of the promotor which responds solely to anaerobiosis has been isolated and by comparison with other anaerobically-regulated promoters a consensus FNR-binding site was identified (Bell et al, Nucl. Acids. Res. 17, 3865–3874, 1989; Jayaraman et al, Nucl. Acids Res. 17, 135–145, 1989). It was also shown that the distance between the putative FNR-binding site and the -10 homology region is critical (Bell et al, Molec. Microbiol. 4, 1753–1763, 1990). It is therefore preferred to use only that part of the nirB promoter which responds solely to anaerobiosis. As used herein references to the nirB promoter refer to the promoter itself or a part or derivative thereof which is capable of promoting expression of a coding sequence under anaerobic conditions. The sequence which we have in fact used and which contains the nirB promoter is:

AATTCAGGTAAATTTGATGTACAT-
CAAATGGTACCCCTTGCTGAATCGTTAAGGTA
GGCGGTAGGCC (SEQ ID NO:1)

An attenuated bacterium according to the present invention may be prepared by transforming an attenuated bacterium with a DNA construct comprising a promoter whose activity is induced by anaerobic conditions, such as the nirB promoter, operably linked to a DNA sequence encoding a heterologous protein. Any suitable transformation technique may be employed, such as electroporation. In this way, an attenuated bacterium capable of expressing a protein heterologous to the bacterium may be obtained. A culture of the attenuated bacterium may be grown under aerobic conditions. A sufficient amount of the bacterium is thus prepared for formulation as a vaccine, with minimal expression of the heterologous protein occurring.

The DNA construct is typically a replicable expression vector comprising the nirB promoter operably linked to a DNA sequence encoding the heterologous protein. The nirB promoter may be inserted in an expression vector, which already incorporates a gene encoding the heterologous protein, in place of the existing promoter controlling expression of the protein. The expression vector should of course be compatible with the attenuated bacterium into which the vector is to be inserted.

The expression vector is provided with appropriate transcriptional and translational control elements including, besides the nirB promoter, a transcriptional termination site and translational start and stop codons. An appropriate ribosome binding site is provided. The vector typically comprises an origin of replication and, if desired, a selectable marker gene such as an antibiotic resistance gene. The vector may be a plasmid.

An attenuated bacterium of the invention can be used as a vaccine. The vaccine comprises a pharmaceutically acceptable carrier or diluent and, as active ingredient, the attenuated bacterium.

The vaccine is advantageously presented in a lyophilised form, for example in a capsular form, for oral administration to a patient. Such capsules may be provided with an enteric coating comprising, for example, Eudragate "S", Eudragate "L", Cellulose acetate, cellulose phthalate or hydroxypropylmethyl cellulose. These capsules may be used as such, or alternatively, the lyophilised material may be reconstituted prior to administration, e.g. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramammary.

The attenuated bacterium of the invention may be used in the prophylactic treatment of a host, particularly a human host but also possibly an animal host. An infection caused by a microorganism, especially a pathogen, may therefore be prevented by administering an effective dose of an attenuated bacterium according to the invention. The bacterium then expresses a heterologous protein capable of raising antibody to the microorganism. The dosage employed will be dependent on various factors including the size and weight of the host, the type of vaccine formulated and the nature of the heterologous protein. However, for attenuated *S.typhi* a dosage comprising the oral administration of from $10^9$ to $10^{11}$ *S.typhi* organisms per dose is generally convenient for a 70 kg adult human host.

The following Example illustrates the invention.

BRIEF DESCRIPTION OF THE DRAWINGS

FIG. 5 shows anti-tetanus toxin fragment C titres of mouse sera. The x-axis shows the types of bacteria used to challenge the mice. The number of doses is shown in brackets. The y-axis denotes absorbance readings at 492 nm.

EXAMPLE

Construction of pTETnir15

Figure 1:
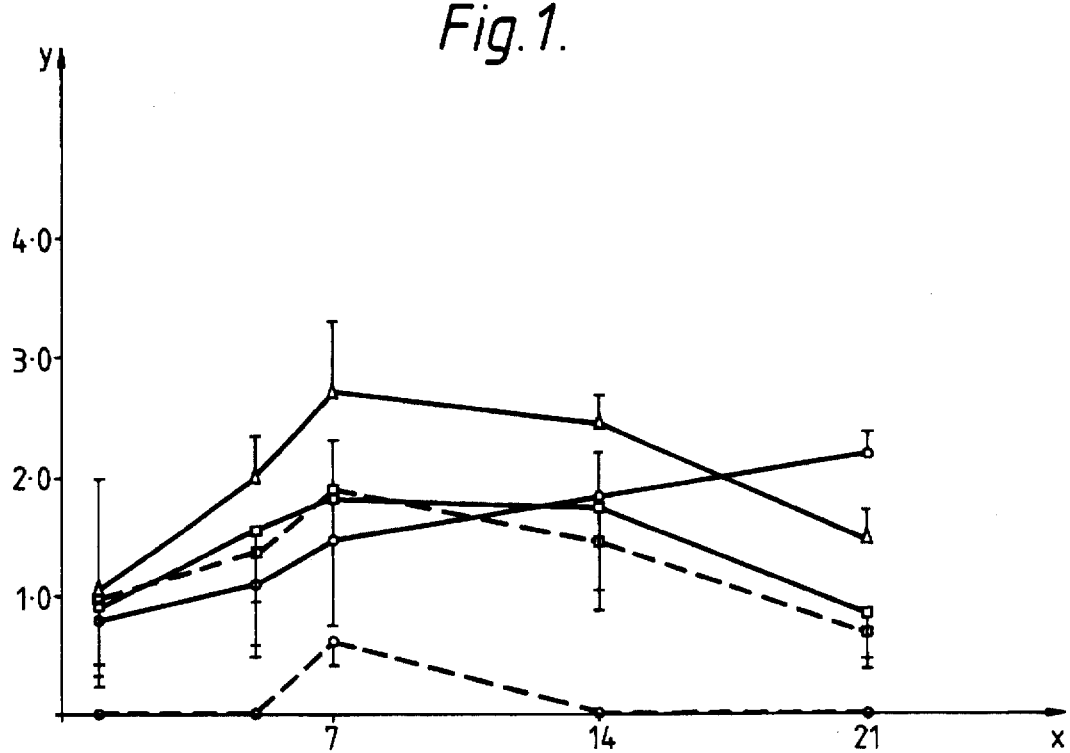
FIGS. 1 to 4 show the abilities of isolates of *S.typhimurium* to grow in vivo in the liver, spleen, Peyers patches and mesenteric lymph nodes respectively of BALB/c mice. The x-axis denotes days after infection, the y-azis denotes $\log_{10}$ viable organisms per organ, Δ denotes isolate BRD509, □ denotes isolate BRD847, o denotes isolate BRD743, — denotes no ampicillin and - - - denotes ampicillin added.
Figure 2:
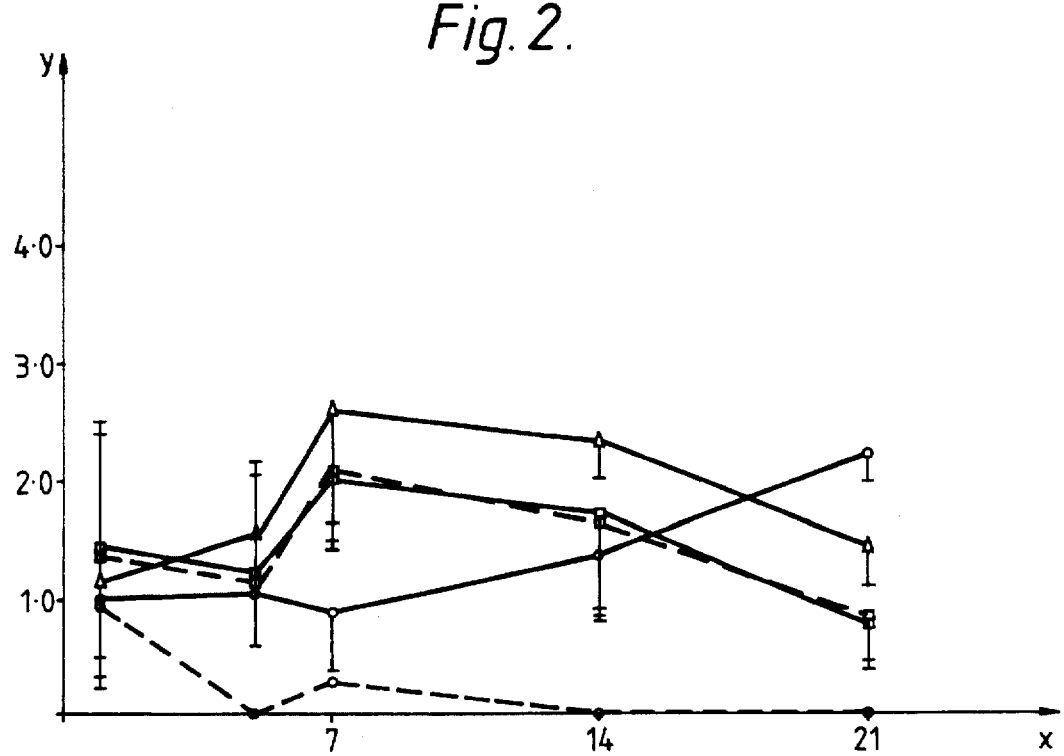
Figure 3:
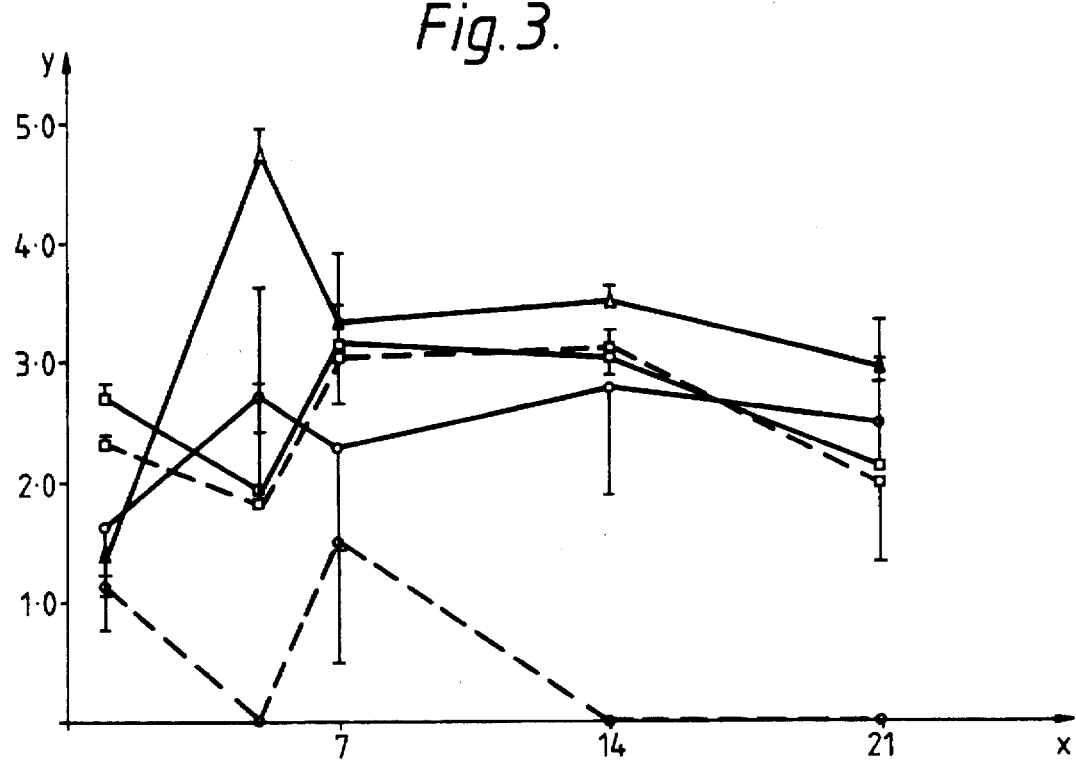
Figure 4:
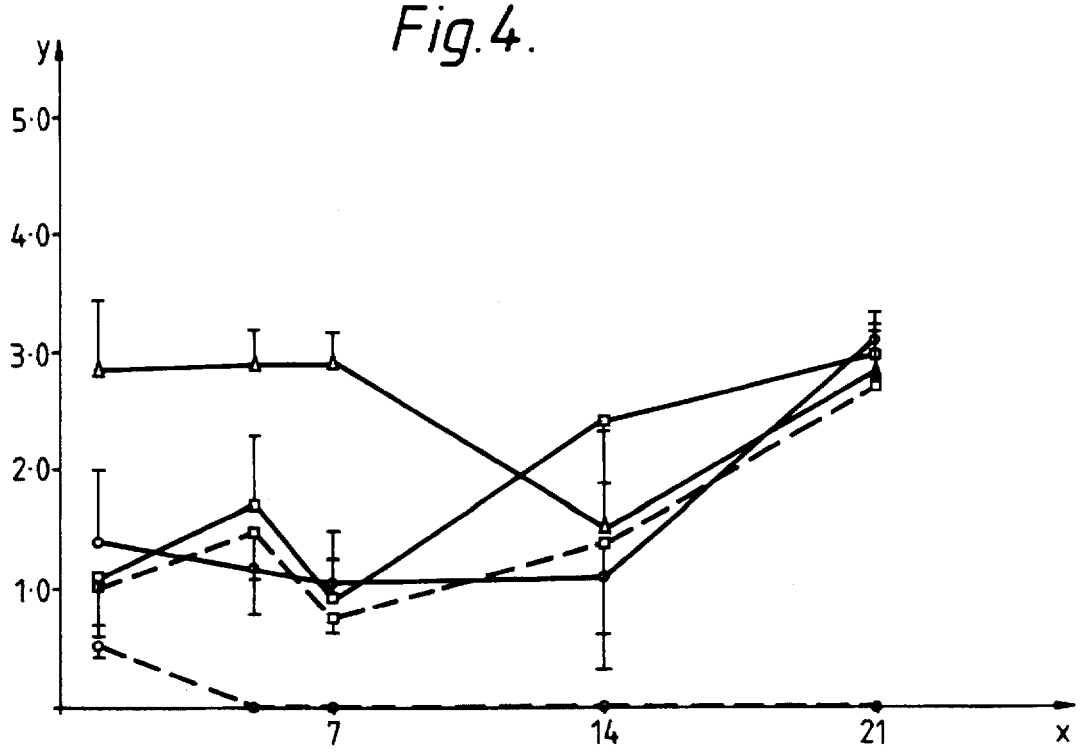

Expression plasmid pTETnir15 was constructed from pTETtac115 (Makoff et al, Nucl. Acids Res. 17 10191–10202, 1989) by replacing the EcoRI-ApaI region (1354 bp) containing the lacI gene and tac promoter with the following pair of oligos 1 and 2:

Oligo-1 5'-AATTCAGGTAAATTTGAT- GTACAT-
CAAATGGTACCCCTTGCTGAATC

Oligo-2 3'-GTCCATTTAAACTACAT- GTAGTTTAC-
CATGGGGAACGACTTAG
GTTAAGGTAGGCGGTAGGGCC-3'(SEQ ID NO:1)
CAATTCCATCCGCCATC-5'(SEQ ID NO:2)

The oligonucleotides were synthesized on a Pharmacia Gene Assembler and the resulting plasmids confirmed by sequencing (Makoff et al, Bio/Technology 7, 1043–1046, 1989).

Construction of SL1334 aroA aroD Harbouring pTETnir15

In order to construct a Salmonella vaccine strain expressing tetanus toxin fragment C under the control of the nirB promoter, an intermediate strain, *S.typhimurium* LB5010 ($r^{-m+}$) (Bullas and Ryo, J. Bact. 156, 471–474, 1983), was transformed with pTETnir15. Colonies expressing fragment C were detected by antibiotic selection followed by colony immunoblotting with anti-tetanus toxin fragment C sera. Colonies were grown overnight on nitrocellulose filters aerobically and then induced by incubating under anaerobic conditions for four hours prior to immunoblotting. One strain that was stably expressing fragment C was used to prepare plasmid DNA. This was used to transform an isolate of S.typhimurium SL1344 aroA aroD designated BRD509 by electroporation. A strain that was stably expressing fragment C (checked by immunoblotting as described above) was chosen for the in vivo studies and was designated BRD847.

Comparison of In Vivo Kinetics of BRD743 and BRD847 in BALB/c Mice

The ability of BRD743 (BRD509 harbouring pTET85) and of BRD847 to grow in vivo was compared after oral administration to BALB/c mice. pTET85 was constructed from pTETtac115 (Makoff et al, Nucl. Acids Res. 17, 10191–10202, 1989) by deleting the 1.1 kb EcoRI fragment carrying the lacI gene. This resulted in the constitutive expression of fragment C in Salmonella strains. Numbers of bacteria were enumerated in livers, spleens, Peyers patches and mesenteric lymph nodes. The bacteria isolated from mice were also assessed for their ability to grow on plates containing ampicillin as an indicator of the percentage of organisms still retaining the plasmid expressing fragment C. The results are shown in FIGS. 1 to 4.

When similar initial numbers of organisms ($5\times10^9$) were used to infect mice it was found that both BRD743 and 847 were able to invade into and persist in all the murine tissues examined but at a lower level than BRD509. However, the intersting feature is that the number of ampicillin resistant organisms obtained from mice infected with BRD743 decreases rapidly and all organisms recovered were ampicillin sensitive by day 14. This indicates that in vivo selection rapidly results in the loss of pTET85 from the Salmonella vaccine strain. In contrast, counts with and without ampicillin for BRD847 were essentially the same for the time the infections were monitored. This demonstrates the added advantage of pTETnir15 in the *S.typhimurium* vaccine strain resulting in organisms with the potential to express fragment c in vivo for a longer period of time with obvious advantages in terms of immunogenicity.

Immunisation of BALB/c Mice Using Salmonella Strains Harbouring pTET85 (BRD743) or pTETnir15 (BRD847)

Groups of twenty mice were incubated orally with $5\times10^9$ cells per mouse of either BRD743, BRD847 or BRD509. On day 25 sera were collected from all mice and analysed by ELISA for anti-tetanus antibodies. All mice vaccinated with BRD847 had detectable anti-fragment C antibody at 25 days whereas those vaccinated with BRD743 or BRD509 did not (FIG. 5). On day 25 ten mice from each group were boosted by oral inoculation with a similar amount of homologous organisms. ELISA analysis of the serum taken from these mice at day 46 showed that the anti-fragment C responses had been boosted for groups inoculated with BRD743 and BRD847. The titres for those mice boosted with BRD847 was significantly higher than for those mice boosted with BRD743. Mice boosted orally with BRD509 failed to produce a detectable antibody response to fragment C.

Tetanus Toxin Challenge of Mice Orally Immunised with BRD847 and 743

The mice vaccinated orally with BRD743, 847 and 509 were tested for immunity against tetanus toxin challenge after one or two doses of the immunising strain. Groups of twenty mice received one single oral dose of $5\times10^9$ organisms and groups of ten mice were challenged on day 25 with 500 50% lethal doses of tetanus toxin (see Table 1). Mice vaccinated with BRD847 were completely protected against challenge after a single oral dose whereas those vaccinated with BRD743 were only partially protected (2/10 survivors). The remaining groups of 10 mice received a second dose of organisms ($5\times10^9$) on day 25 and were challenged on day 46 (after the 1st dose). Again mice immunised with BRD847 were completely protected after challenge with tetanus toxin whereas those immunised with BRD743 were only partially protected (5/10). Mice immunised with 1 or 2 doses of BRD509 and challenged with tetanus stoxin all died. BRD847 is an effective single dose oral vaccine against tetanus toxin challenge in mice. Groups of mice were also challenged with tetanus toxin after receiving 1 and 2 intravenous doses of $10^5$ organisms of BRD847 and BRD743. All mice were fully protected against challenge with tetanus toxin after 1 or 2 doses of vaccine strain.

TABLE 1

Oral immunisation of mice against tetanus using *S. typhimurium* SL1344 aroA aroD pTET85 and *S. typhimurium* SL1344 aroA aroD pTETnir15

| Vaccine | Dose | No. Doses | No. of mice surviving tetanus challenge |
|---|---|---|---|
| SL1344 aroA aroD | $8.6 \times 10^9$ | 1 | 0/10 |
| (BRD509) | $7.4 \times 10^9$ | 2 | 0/10 |
| SL1344 aroA aroD | $6.4 \times 10^9$ | 1 | 2/10 |
| pTET85 (BRD743) | $8.2 \times 10^9$ | 2 | 5/10 |
| SL1344 aroA aroD | $9.5 \times 10^9$ | 1 | 10/10 |
| pTETnir15(BRD847) | $7.5 \times 10^9$ | 2 | 9/9 |

We claim:

1. A method for prophylactically treating a host against infection by a microorganism, which method comprises administering to the host an attenuated *Salmonella bacterium* which contains a nirB promoter operably linked to a DNA sequence encoding a heterologous protein, wherein the heterologous protein is expressed in the host and induces in the host an immune response against the microorganism.

2. The method according to claim 1, wherein the bacterium is selected from the group consisting of *Salmonella typhi* and *Salmonella typhimurium.*

3. The method according to claim 1, wherein attenuation of the bacterium is attributable to a non-reverting mutation in a gene in an aromatic amino acid biosynthetic pathway.

4. The method according to claim 3, wherein the bacterium harbours a non-reverting mutation in each of two discrete genes in the aromatic amino acid biosynthetic pathway.

5. The method according to claim 4, wherein the bacterium is selected from the group consisting of aroA aroC, AroA aroD and aroA aroE mutants.

6. The method according to claim 1, wherein the heterologous protein comprises an antigenic sequence from an organism selected from the group consisting of viruses, bacteria, fungi, yeasts and parasites.

7. The method according to claim 6, wherein the heterologous protein is selected from the group consisting of the P.69 protein from *Bordetella pertussis* and tetanus toxin fragment C.

* * * * *